United States Patent [19]

Anderson et al.

[11] Patent Number: 4,921,503

[45] Date of Patent: May 1, 1990

[54] NOVEL DYEING SYSTEM

[75] Inventors: James S. Anderson, Danbury, Conn.; Thomas M. Schultz, Highland Mills, N.Y.

[73] Assignee: Clairol Incorporated, New York, N.Y.

[21] Appl. No.: 243,525

[22] Filed: Sep. 12, 1988

[51] Int. Cl.$^5$ .................. A61K 7/13; C07D 209/36
[52] U.S. Cl. ........................... 8/408; 8/405; 8/406; 8/409; 8/429; 548/485
[58] Field of Search .............. 8/408, 409, 423, 429, 8/414; 548/485

[56] References Cited

U.S. PATENT DOCUMENTS

| | | | |
|---|---|---|---|
| 1,157,485 | 10/1915 | Wray . | |
| 2,163,094 | 6/1939 | Kambli | 548/485 |
| 2,642,439 | 6/1953 | Coles | 548/485 |
| 3,733,175 | 5/1973 | Alperin et al. | 8/414 |
| 4,695,285 | 9/1987 | Chung-Bong-Chan et al. | 8/429 |
| 4,750,908 | 6/1988 | Rosenbaum et al. | 8/429 |

OTHER PUBLICATIONS

Elderfield, Heterocyclic Compounds-vol. 3, 1952, p. 218.
Chem.Abs.—: 117655g re: Ballentine et al. article in Org. Mass. Spectrom, (1971) 5 (8), 1003–14.
Chem. Abs—: 2928e re: Kosturiak et al. article in Petrochemia 1973, 13 (4), 120-6.
Chem. Abs.—: 65375b re: Kosturiak et al. article in Petrochemia, 1973, 13(1), 30-5.
Hetrocyclic Compounds R. C. Elderfield ed., John Wiley & Sons (1952) p. 218.
F. Popp, J. Heterocyclic Chem., 1969, v. 6, pp. 125–127.
F. Popp et al., J. Heterocyclic Chem., 1971, v. 8, pp. 473–475.
M. Rajopadhye et al., J. Heterocyclic Chem., 1981, v. 24, pp. 1637–1642.

Primary Examiner—A. Lionel Clingman
Assistant Examiner—J. Darland
Attorney, Agent, or Firm—S. M. Nolan

[57] ABSTRACT

Substituted 3-aryl amino-indoline-2-ones, produced by the reaction of certain isatins and amines are among a group of compounds useful as hair colorants. The hair itself appears to function as a dye-formation promoter, so that no oxidative reagents are needed.

13 Claims, No Drawings

NOVEL DYEING SYSTEM

BACKGROUND

Conventional hair dyeing practice involves either the diffusion of a dye into the hair (temporary or semi-permanent coloring) or a chemical reaction between two (or more) organic compounds within the hair fiber to develop a new and larger colored material. While the former method gives poorly lasting results, the latter process yields more permanent and durable dyeings. Unfortunately, this second type of hair dyeing typically requires a strong oxidant such as hydrogen peroxide, which can lead to substantial hair damage.

It has long been the aim of cosmetic chemists and hair colorists to combine the benefits of both methods into a single product. That is, to have a long lasting dye formed in the hair without the concurrent damage associated with oxidative dyeing.

Isatin has been claimed as a direct hair dye, alone or in combination with quinone dyes and involving no chemical reaction (U.K. Patent application GB 2 181 750A). The isatin is unchanged in the process and only dyes yellow.

Another isatin claimed as useful in hair coloring (German Offen. 2 716 671) is diaminoisatin for use in oxidative dyeing. This compound can only be used in the presence of a strong oxidant that causes coupling with a 1,4-disubstituted benzene intermediate to produce color.

Certain derivatives of isatin have been taught in the literature. U.S. Pat. No. 3,374,262 to Seefelder, et al. and U.S. Pat. No. 3,665,029 to Boerth show the production of ortho-aminobenzonitriles by the thermal decomposition of isatin-beta-oximine. The nitriles are described as intermediates and starting materials for dyes.

U.S. Pat. No. 3,558,646 to Buderlein, describes the production of 2- oxo-3-indolinylidene hydrazides as anti-convulsant and inflammatory drugs.

None of these disclosures describe the use of 3-arylimino-indoline-2-ones for coloring keratinaceous fibers, specifically human hair.

The actual materials used in this invention, 3-arylimino-indoline-2-ones, are described in CA79:65375b, CA81:2928e, CA75:117655g; J. Heterocyclic Chem., Vol. 6, p. 125 (1969), Vol. 8, p. 473 (1971) and Vol. 24, p. 1637 (1981); and Heterocyclic Compounds, p. 218 ff (Elderfield, ed., 1952). Notably, in each and every description there is no mention of the dyeing capabilities of these compounds. Also, the novelty of the instant invention, the formation of the dyes by the catalytic action of hair has been heretofore unknown.

THE INVENTION

Applicants have discovered a hair dyeing system which uses the hair fiber itself to serve as a dye-forming promoter. This system encompasses the fundamental aspects of the conventional permanent hair coloring system, that is, the reaction of two (or more) organic compounds which combine to form a bright and intensely colored dye within the hair fiber. However, no oxidative reagents are required to develop the color. The dyes of this invention are 3-arylimino-indoline-2-ones.

Furthermore, applicants have found that aromatic amines can be contacted with an isatin in the presence of hair either together or sequentially to yield shampoo and light stable, long-lasting colorings.

Additionally, the same dyes may be synthesized and applied directly to the hair give a moderate color impartation similar to semi-permanent-type hair colorants.

The invention is concerned with novel processes of coloring hair using certain compounds and compositions containing these compounds and/or their precursors.

ADVANTAGES

The processes and compositions of the invention have several advantages over conventional agents, techniques and formulations for coloring keratinaceous fibers.

The compounds of the invention, whether pre-prepared or formed in-situ in or on the hair or other keratinaceous substrate to be colored give dyeings without the addition of oxidizing agent(s) or the use of pH adjustment(s). The non-requirement of any oxidizing agents significantly reduces any chance of damaging the hair fibers. In addition, the proteinaceous and disulfide bonds of the hair are less likely to be damaged by avoiding pH extremes and by performing the process around neutrality. The dyeing is generally carried out in about 20 to about 40 minutes.

Furthermore, the dyes color cosmetically-treated hair and virgin hair equally well, unlike conventional colorants where uneven dyetake often occurs on different substrates.

In addition, the dyes produced using the instant invention do not color effectively in the absence of hair. Thus, if either or both reactant(s) or the preformed dye spills or splashes onto skin, it can be wiped or washed away easily without staining, so long as prolonged contact with the skin (i.e., about 20 minutes or more) has not occurred.

The processes and compositions of the invention have several advantages over conventional agents, techniques and formulations for coloring keratinaceous fibers. Furthermore, the fact that additional reagents or catalysts are not needed means that virtually no damage can occur to the hair during the course of normal use of the invention. In fact, the hair is usually lustrous in appearance following dyeing in accordance with the invention.

These and other advantages, as well as other aspects, of the invention will be apparent after a consideration of the following description.

DESCRIPTION OF THE INVENTION

The invention deals with processes and compositions for coloring keratinaceous substrates. Both use certain compounds or the reaction products thereof.

Compounds

The compounds used in the invention are: (A) an isatin of formula I as follows:

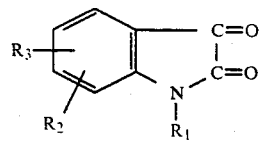

(I)

wherein $R_1$ is independently H, $C_{1-6}$ alkyl, acetyl, benzoyl, or phenyl; $R_2$ and $R_3$ are each independently H or $C_{1-6}$ alkyl, OH, $NH_2$, Halogen, $NO_2$, $C_{1-6}$ alkyl phenyl, phenyl, $C_{1-6}$ alkoxyhydroxy alkoxy, polyhydroxy alkyl, alkyl amino, hydroxy alkylamino, polyhydroxy alkyl-amino (all are $C_{1-6}$ poly hydroxy 1-6 hydroxy group); and (B) an amine of formula II as follows:

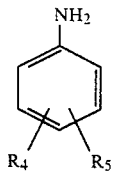

(II)

wherein $R_4$ and $R_5$ are each independently H, halogen, alkyl, phenyl, substituted phenyl, hydroxy, alkoxy, trifluoromethyl, nitro, amino, monoalkylamino, dialkylamino, monohydroxyalkyl amino, poly-hydroxyalkyl amino, aniline, bis(monohydroxyalkyl)amine, bis(-polyhydroxyalkyl)amino or $C_{1-6}$ carboxyaldehyde, wherein all alkyl groups contain from about 1 to about 6 carbon atoms.

In the case of amine reactants of formula II, the resulting compounds generally conform to formula III:

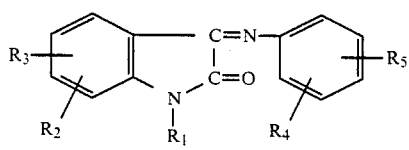

(III)

wherein $R_1$, $R_2$, $R_3$, $R_4$ and $R_5$ have the meaning given above. These are substituted 3-arylimino-indoline-2-ones.

While the isatin and amine reactants are generally used in stoichiometric proportions, i.e., about 1:1, the use of an excess of either is contemplated. Generally ratios of isatin to amine will vary from about 1:4 to about 4:1, preferably about 1 to about 1.5

The isatin and arylamine components are generally brought together, whether or not hair is present, in at least one suitable diluent. Useful diluents are preferably solvents for one or more of the reagent(s) and the resultant dye. Suitable solvents include alcohols such as ethanol, isopropanol, and the like. Mixtures are operable.

Alternatively, these compounds may be contacted in dispersion in one or more non-solvent(s). When such systems are employed, one or more surfactants and/or other conventional dispersing aids are employed. The reactants may be dispersed in media such as xanthan gum and the like. Mixtures can be used.

Suitable surfactants and dispersion aids for such systems include sodium lauryl sulfate, alpha-olefin sulfonate and the like. Mixtures are contemplated.

Unless stated otherwise, all percentages given herein are weight percents, based on total composition weight.

DYEING PROCESSES

There are two separate methods of coloring the hair or other substrates with 3-arylimino-indoline-2-ones. The first method is the application of the preformed dye in solution directly to hair. The second method is the process of combining isatin with arylamine compounds on hair to form the dyes in-situ. Typical embodiments of these two methods are described below.

Method A:

This first method of coloring the hair involves applying the previously-prepared 3-arylimino-indoline-2-ones to the hair in a suitable medium. A general synthetic procedure is detailed by way of example of obtaining these dyes, but is not intended to limit in any way the scope or breadth of such compounds that may be useful in the practice of this method of hair coloring.

The dyes can be synthesized in the following manner: 0.5 moles isatin + 0.51 moles arylamine + 150 ml toluene are refluxed and $H_2O$ is azeotroped off. When TLC shows no isatin, the suspension is cooled in an ice-bath, then filtered and washed (3×50 ml) with toluene. The product is dried under vacuum at 50° C. Yields are 90-100%.

Table I gives the spectrophotometric properties of several examples of compounds of structure III in 95% ethanol.

TABLE I

| $R_1$ | $R_2$ | $R_3$ | $R_4$ | $R_5$ | λmax (nm) | log — |
|---|---|---|---|---|---|---|
| H | H | H | H | H | 409 | 3.29 |
| H | H | H | H | 4-OH | 444 | 3.60 |
| H | H | H | H | 4-$NH_2$ | 486 | 3.88 |
| H | H | H | H | 4-N($CH_2CH_2OH$)$_2$ | 528 | 3.81 |
| H | H | H | H | 4-NH$C_6H_5$ | 506 | 4.02 |
| H | H | H | H | 4-$OCH_3$ | 436 | 3.57 |
| H | H | H | H | 2-$CF_3$ | 408 | 3.09 |
| H | H | H | H | 3-$NO_2$ | 409 | 3.39 |
| H | H | H | 2-$OCH_3$ | 4-$OCH_3$ | 454 | 3.50 |
| H | 5-CL | 7-CL | H | 4-OH | 464 | 3.79 |
| H | H | 5-$NO_2$ | H | 4-$NH_2$ | 508 | 3.51 |

Hair dyeing is performed by dissolving the 3-aryliminoindoline-2-one at a concentration of 0.25% in a common hair color base and immersing the hair for 30 minutes, then rinsing with tap water and drying.

When using Method A, the solution is generally contacted with the hair for a period of from about 5 to about 40 minutes, preferably about 20 to about 30 minutes. Longer times are contemplated, but do little to enhance the final dyeout. Shorter times may be used to produce various color effects, such as when a shading or more gentle coloring is desired.

It is important to note that for effective coloration to occur, the colorants should be contacted with keratinaceous fibers, e.g. hair or wool, preferably human hair. However, the dyes have no affinity for skin; thus no scalp staining occurs.

In addition, dyeings can be carried out with wool, silk, cellulose fiber, e.g. cotton, or polymer fibers, e.g. polyamides, polyesters, polyacetate and the like.

Method B:

Hair can be dyed more intensely than described in Method A by forming the 3-arylimino-indoline-2-ones in-situ. This is accomplished simply by treating hair with a solution of isatin and an arylamine and allowing dye formation to occur. Quite remarkably, color development occurs quickly on the hair but slowly, if at all, in the solution. This results in complete, even coverage of the fiber with no skin staining during the dyeout. The hair has smooth feel and excellent lustre. The isatin/amine solution typically does not change color during the dyeout regardless of the type of hair, and color development occurs exclusively on the fiber.

For example, 1g isatin and 1g p-phenylenediamine are dissolved in 30 ml ethanol, then 70 ml water is added to give a solution of 1% (wt/vol) of each reactant. This solution is then applied to any type of hair, virgin or cosmetically treated, for 20 minutes and then rinsed off with tap water; a red dyeout is obtained.

Table II gives examples of the colors obtained on various hair types and with various arylamines. Table III gives some examples of the effect of combining isatin with two or more arylamines. The resulting combination of colors makes a wide range of shades possible. The values are quantitative measures of the light reflectivity (L=100 is white; L=0 is black) and color (+a=red; −a=green; +b=yellow; −b=blue).

The in-situ formation of the 3-arylimino-indoline-2-ones can also be achieved by the sequential application of the reactants in any order. For example, commercially bleached hair is soaked in an aqueous ethanol solution of 1% (wt/vol) isatin for 5 minutes and then a 1% (wt/vol) solution of 4-aminophenol added to color the hair a bright yellow-gold in 20 minutes. Virgin pigmented hair is colored equally well.

Dyeout intensity is proportional to the concentration of the reactants. It is also proportional to the duration of the dyeout.

TABLE II

Colors Obtained with Isatin and Various Arylamines on Different Types of Hair*

| Arylamine | Bleached | Hair Type Blended Grey | Lt. Brown |
|---|---|---|---|
| Ex. 1 4-aminophenol | Dk. yellow | Dk. yellow | Golden-brown |
| Ex. 2 p-phenylenediamine | Red | Dk. Red | Burgundy |
| Ex. 3 4-bis (2-hydroxy-ethyl)aminoaniline | Med. rose | Med. rose | Lt. burgundy |
| Ex. 4 4-dimethylamino-aniline | Violet | Dk. violet | Dk. burgundy |
| Ex. 5 4-aminodiphenyl-amine | Dk. violet | Violet | Dk. burgundy |

*Hair treated 20 minutes with a 1% (wt/vol) solution of each of isatin and arylamine, then rinsed and dried.

The hair dyeing temperature is not critical. Generally, the reaction step and the hair contacting step, whether simultaneous or sequential—i.e., dye contacting hair subsequent to reaction—will take place at ambient or room temperature. While heating to temperatures of about 30° C. to about 50° C. can be used to accelerate reaction and coloration, such heating is not required. Generally temperatures no lower than about 10° C. are operable.

Compositions

The compositions useful in carrying out the invention fall into three categories:

A. Those containing only one of each essential reactant;
B. Those containing the preformed dye; and
C. Those containing both essential reactants in an unreacted state.

Category A compositions are generally liquids containing from about 0.01 to about 5%, probably about 0.25 to about 2.0% of either the isatin or amine reactant. These are generally solutions in aqueous alcohol and/or common hair dye base as carrier(s).

To insure stability, two Category A compositions, one containing isatin and the other amine, are packaged separately and are mixed before or during contact with hair or sequentially applied (e.g., one of the amine or isatin compounds is contacted alone with the hair).

Category B compositions typically contain about 0.1 to about 10%, preferably about 0.5 to about 3.0% of the preformed dye. The same solvent(s) or carriers used for Category A compositions are operable.

Category C compositions are generally solid or semisolid materials which are packaged so that when water, or other suitable diluent, is added, the mixture can then be used to color the hair. These materials generally contain from about 0.01 to about 5.0%, preferably from about 0.25 to about 2.0% of the isatin component and from about 0.01 to about 5.0%, preferably about 0.25 to about 2.0%, of the amine component. Suitable stabilizers and/or coating materials can be used to insure that premature reaction does not occur.

When water or other carrier(s) are employed, they will be present at concentrations of about 10 to about 99.99 wt. %, with concentrations of about 20 to about 80 preferred.

The use of any of a variety of packaging concepts which would insure the stability for future use of Category A and C compositions is contemplated. Thus, liquid/liquid, liquid/solid, liquid/semi-solid combinations and the like may be used.

When solid or semisolid compositions are desired, mousse, gel, cream, powder or other useful form may be employed. Suitable solid carriers or fillers are used in quantities which give the formulation a desired consistency for storage and/or application purposes. Such solid carriers or fillers include carbopol, xanthan gum, and the like. Fillers, when used, are present in amounts of from about 0.1 to about 99.9%, preferably about 5.0% to about 99.5%.

Other conventional additives, e.g. foaming agents, surfactants, perfumes, processing aids, thixotropic agents, etc. can be used in conventional amounts, i.e., in quantities suitable to their functions.

It should be noted, however, that the number of fillers, diluents and other additives should be kept to a minimum to insure the necessary contacting of the reagents or the dye with the keratinaceous surface. It appears that the hair or other substrate acts like a catalyst to produce the desired color. Thus, care must be taken to insure that the formulation—or mixture of formulations when category A compositions are used—is evenly and well distributed on the hair.

Post-treatment of hair

After the dyeing operation is complete, the hair or other keratinaceous fiber which has been colored can be rinsed to remove excess reagent(s) or dye.

Following the rinsing operation, alkaline hydrogen peroxide or reducing agents may be used to modify the dyeouts. For example, reducing agents decrease the intensity of the colors.

TABLE III

Method B was used to dye virgin, medium-brown hair. Ethanol/water solution of isatin and various amines were applied to swatches.

| Amine(s) (wt %) | Color | L,a,b |
|---|---|---|
| Ex. 6 4-bis(2-hydroxyethyl) aminoaniline (0.5%) p-phenylenediamine (0.25%) pH 8.5 | Auburn | 18.24, 9.69, 5.20 |
| Ex. 7 p-phenylenediamine (0.25%) 4-aminophenol (0.25%) pH 5.8 | Lt. auburn | 22.11, 0.87, 8.13 |
| Ex. 8 4-bis(2-hydroxyethyl) aminoaniline (0.35%) p-phenylenediamine (0.15%) | Med. auburn | 19.63, 8.98, 6.17 |

TABLE III-continued

Method B was used to dye virgin, medium-brown hair.
Ethanol/water solution of isatin and various amines
were applied to swatches.

| | Amine(s) (wt %) | Color | L,a,b |
|---|---|---|---|
| 9 | 4-aminophenol (0.1%) pH 6.3 4-bis (2-hydroxyethyl) aminoaniline (0.5%) pH 6.4 | Pale violet | 20.26, 6.39, 4.34 |

*Hair dyed with 0.5% isatin + amine in 30% ethanol-water.

Reasonable variations, such as those which would occur to a skilled artisan, can be made herein without departing from the scope of the invention.

We claim:

1. A process for dyeing a keratinaceous substrate comprising the step of contacting it with a formulation containing at least one compound of formula:

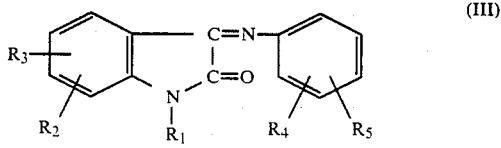

$R_1$ through $R_5$ being defined below wherein the compound is produced via the reaction of (a) at least one compound of formula I:

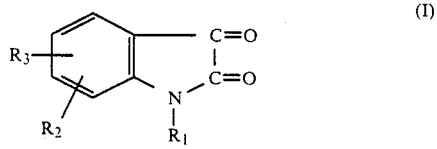

wherein $R_1$ is independently H, alkyl, acetyl, benzoyl or phenyl; and $R_2$ and $R_3$ are each independently H, alkyl, OH, $NH_2$, halogen, $NO_2$, alkylphenyl, phenyl, alkoxy, hydroxyalkoxy, polyhydroxyalkyl, alkylamino, hydroxyalkylamino or polyhydroxyalkylamino wherein all alkyl groups contain from about 1 to about 6 carbon atoms; with (b) at least one reactant which is of formula II:

wherein $R_4$ and $R_5$ are independently H, alkyl, phenyl, substituted phenyl, hydroxy, alkoxy, trifluoromethyl, nitro, amino monoalkylamino, dialkylamino, monohydroxyalkyl amino, polyhydroxyalkyl amino, anilino bis(monohydroxy-alkyl)amine bis(monohydroxyalkyl)amino, bis(monohydroxyalkyl)amino or carboxyaldehyde, wherein all alkyl groups contain from about 1 to about 6 carbon atoms; wherein the contacting step involves the use of (a) and (b) either simultaneously or sequentially.

2. The process of claim 1 wherein (a) and (b) are contacted with the substrate simultaneously.

3. The process of claim 1 wherein reactant (a) is contacted with the substrate first, with subsequent use of reactant (b).

4. The process of claim 1 wherein reactant (b) is contacted with the substrate first, with subsequent use of reactant (a).

5. The process of claim 1 wherein reactants (a) and (b) are premixed and then contacted with the substrate.

6. A process for dyeing a keratinaceous substrate comprising the steps of (1) reacting (a) and (b) of claim 1 under suitable conditions and (2) contacting the reaction product with the substrate.

7. A hair-dyeing composition which comprises a mixture of reactants (a) and (b) or the reaction product of (a) and (b), wherein (a) is at least one reactant which is a compound of formula I:

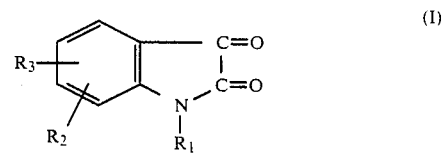

wherein $R_1$ is independently H, alkyl, acetyl, benzoyl or phenyl; and $R_2$ and $R_3$ are each independently H, alkyl, OH, $NH_2$, halogen $NO_2$, alkylphenyl, phenyl, alkoxy, hydroxyalkoxy, polyhydroxyalkyl, alkylamino, hydroxyalkylamino or polyhydroxyalkylamino wherein all alkyl groups contain from about 1 to about 6 carbon atoms; with (b) at least one reactant which is of formula II:

wherein $R_4$ and $R_5$ are independently H, alkyl, phenyl, substituted phenyl, hydroxy, alkoxy, trifluoromethyl, nitro, amino, monoalkylamino, dialkylamino, monohydroxyalkyl amino, polyhydroxy-alkyl amino, anilino, bis(monohydroxyalkyl)amino, bis(polyhydroxyalkyl)amino or carboxyaldehyde wherein all alkyl groups contain from about 1 to about 6 carbon atoms, and wherein the reaction product of (a) and (b) is of formula III:

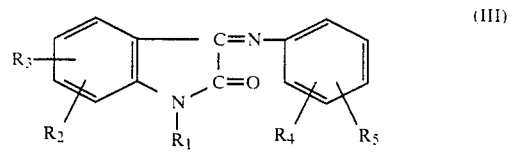

with $R_1$ through $R_5$ being defined above.

8. The composition of claim 7 containing a mixture of reactants (a) and (b) and at least one suitable carrier.

9. The composition of claim 7 containing the reaction product of (a) and (b) and at least one suitable carrier.

10. The composition of claim 7 containing at least one compound of formula III:

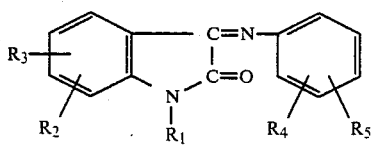 (III)

wherein $R_1$, $R_2$, $R_3$, $R_4$ and $R_5$ have the meanings given in claim 7.

11. A hair dyeing kit comprising:
(a) a first package containing, in a suitable carrier, an isatin reactant of formula I:

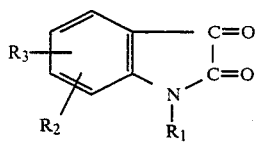 (I)

wherein $R_1$ is independently H, alkyl, acetyl, benzoyl or phenyl; and $R_2$, and $R_3$ are each independently H, alkyl, OH, $NH_2$, halogen, $NO_2$, alkylphenyl, phenyl, alkoxy, hydroxyalkoxy, polyhydroxyalkyl, alkylamino, hydroxyalkylamino or polyhydroxyalkylamino wherein all alkyl groups contain from about 1 to about 6 carbon atoms; and
(b) a second package containing, in a suitable carrier, an amine reactant of formula II:

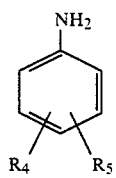 (II)

wherein $R_4$ and $R_5$ are independently H, alkyl, phenyl, substituted phenyl, hydroxy, alkoxy, trifluoromethyl, nitro, amino, monoalkylamino, dialkylamino, monohydroxyalkyl amino, polyhydroxyalkyl amino, anilino, bis(monohydroxyalkyl)amino, bis(polyhydroalkyl) amino or carboxyaldehyde, wherein all alkyl groups contain from about 1 to about 6 carbon atoms.

12. The kit of claim 11 wherein the second package contains at least one reactant of formula II as follows:

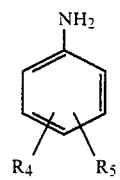 (II)

wherein $R_4$ and $R_5$ are each independently H, halogen, alkyl, phenyl, substituted phenyl, hydroxy, alkoxy, trifluoromethyl, nitro, amino, monoalkylamino, dialkylamino, monohydroxyalkyl amino, poly-hydroxyalkyl amino, aniline, bis(monohydroxyalkyl)amine, bis(polyhydroxyalkyl)amino or $C_{1-6}$ carboxyalkehyde, wherein all alkyl groups contain from about 1 to about 6 carbon atoms.

13. A hair dyeing kit comprising, in a suitable carrier, at least one 3-arylimine-indoline-2-one produced by the reaction of (a) at least one compound of formula I:

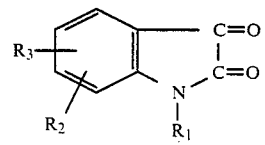 (I)

wherein $R_1$ is independently H, $C_{1-6}$ alkyl, acetyl, benzoyl or phenyl; and $R_2$ and $R_3$ are each independently H, alkyl, OH, $NH_2$, halogen, $NO_2$, alkylphenyl, phenyl, alkoxy, hydroxyalkoxy, polyhydroxyalkyl, alkylamino hydroxyalkylamino or polyhydroxyalkylamino wherein all alkyl groups contain from about 1 to about 6 carbon atoms; with (b) at least one reactant which is of formula II:

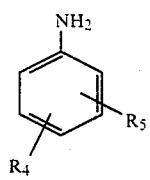 (II)

wherein $R_4$ and $R_5$ are independently H, alkyl, phenyl, substituted phenyl, hydroxy, alkoxy, trifluoromethyl, nitro, amino monoalkylamino, dialkylamino, monohydroxyalkyl amino, polyhydroxyalkyl amino, anilino, bis(monohydroxyalkyl)amino, bis(polyhydroxyalkyl)amino or carboxyaldehyde, wherein all alkyl groups contain from about 1 to about 6 carbon atoms.

* * * * *